United States Patent [19]
Tamba et al.

[11] Patent Number: 4,812,288
[45] Date of Patent: Mar. 14, 1989

[54] NON PRECIOUS NICKEL BASED CHROMIUM CONTAINING ALLOY FOR DENTAL PROSTHESES

[75] Inventors: Alberto Tamba; Silverio Fioravanti, both of Rome; Antonio Scaccia, Veroli, all of Italy

[73] Assignee: Centro Sviluppo Materiali S.p.A., Rome, Italy

[21] Appl. No.: 141,612

[22] Filed: Jan. 5, 1988

[30] Foreign Application Priority Data

Jan. 9, 1987 [IT] Italy ............................... 47511 A/87

[51] Int. Cl.$^4$ .............................................. C22C 19/05
[52] U.S. Cl. ...................................... 420/443; 433/207
[58] Field of Search ............... 420/443; 148/427, 428; 433/207

[56] References Cited

U.S. PATENT DOCUMENTS 4,749,546  6/1988  Burley .................... 420/443

Primary Examiner—R. Dean
Attorney, Agent, or Firm—Young & Thompson

[57] ABSTRACT

A Ni-Cr based alloy not containing precious metals has been developed for prosthetic dentistry uses. The alloy is characterized by high hardness, good workability, high corrosion resistance and optimal adherence to ceramic materials, and consists essentially of:

| | |
|---|---|
| Cr | 22.0–25.0% weight |
| Mo | 5.5–7.5% weight |
| Si | 2.0–4.5% weight |
| B | 0.25–0.50% weight |
| Al | ≦0.2% weight |
| Fe | ≦0.5% weight |
| C | ≦0.05% weight |
| Cu | ≦0.5% weight |
| Mn | ≦0.5% weight |
| S | ≦0.01% weight |
| Rare earths | 0.005–0.2% weight |
| remainder Ni and impurities. | |

6 Claims, No Drawings

NON PRECIOUS NICKEL BASED CHROMIUM CONTAINING ALLOY FOR DENTAL PROSTHESES

The present invention relates to the development of an alloy for dental prostheses which does not contain precious metals, such as gold, silver or platinum. In dentistry, alloys containing precious metals (gold, silver, platinum, palladium) are used all over the world for making dental prostheses.

These alloys, however, do not posses high stiffness and, as a result, have a limited fatigue strength which gives rise to difficulties when full dentures have to be made. In addition, these alloys have the obvious disadvantage of being extremely expensive. In recent years, therefore, research has been concentrated on the development of equivalent alloys not containing precious metals.

Nickel based chromium containing alloys have proved the most promising in this connection, providing valid substitutes for precious metal alloys both from the technical and from the economic standpoint. The non precious alloys available today on the market for dentistry are not however entirely satisfactory. Depending on their composition, they exhibit either inferior electrochemical properties (and are therefore not completely biocompatible) or are too hard (and consequently difficult to machine) or not hard enough (and therefore with inadequate mechanical strength). In addition, many of these commercial alloys have a high melting point and require the use of special casting equipment.

Therefore non precious dental alloys were needed with enhanced overall properties as compared with existing alloys and without the inclusion of toxic elements (such as, for instance, gallium, cadmium and above all beryllium).

A non precious nickel based alloy has now been developed which contains chromium, molybdenum and other alloying elements and which possesses an optimal combination of properties from the standpoint of biocompatibility, machinability and mechanical strength. The alloy also exhibits excellent adherence to the ceramic coating so that it can be used advantageously in association with the latter material.

The present invention relates therefore to the development of an alloy for dental prostheses comprising:

| | | |
|---|---|---|
| Cr | 22.0–25.0 | % weight |
| Mo | 5.5–7.5 | % weight |
| Si | 2.0–4.5 | % weight |
| B | 0.25–0.50 | % weight |
| Al | ≦0.2 | % weight |
| Fe | ≦0.5 | % weight |
| C | ≦0.05 | % weight |
| Cu | ≦0.5 | % weight |
| Mn | ≦0.5 | % weight |
| S | ≦0.01 | % weight |
| Rare earths | 0.005–0.2 | % weight |
| Remainder consisting of Ni and impurities. | | |

Preferably, the alloy of the present invention comprises:

| | | |
|---|---|---|
| Cr | 23.5–24.5 | % weight |
| Mo | 6.2–7.2 | % weight |
| Si | 3.0–4.0 | % weight |
| B | 0.3–0.4 | % weight |
| Al | 0.005–0.1 | % weight |
| Fe + Mn + Cu | ≦1 | % weight |
| C | ≦0.03 | % weight |
| S | ≦0.01 | % weight |
| Rare earths | 0.005–0.15 | % weight |
| Remainder consisting of Ni and impurities. | | |

Preferably, the Ce fraction of the rare earths content ranges between 0.01% and 0.06% by weight. In addition, the alloy is preferably characterized in terms of the contents of certain specific component elements, as expressed by the following mathematical relationships:

(a) $xCr + 3.3 \, yMo \geq 42$ where $x$ = percent weight of Cr present in the alloy
$y$ = percent weight of Mo present in the alloy (b) $1 < \%$ rare earths/ $\%$ S $< 40$ or preferably:

(b') $1 < \%$ Ce/$\%$ S $< 30$

These relationship control the superior resistance of the alloy of the present invention to corrosion by bodily fluids, especially saliva, in which the chlorine ion is the principal agent responsible for local attack. Complete immunity of the alloy to saliva corrosion is ensured when the sum of the chromium and molybdenum per cent weight contents is greater than, or equal to 42. Furthermore, all other conditions being equal, the pitting potential of the alloy of this invention is controlled by the ratio of the rare earth content to the sulfur content and reaches its optimal value when this ratio is in the 10–30 range.

The nature and the contents of the various elements present confer to the alloy of this invention an optimal combination of properties. In fact, the alloy possesses satisfactory biocompatibility characteristics, can be shaped and worked easily and, above all, exhibits excellent adherence to ceramic substrates. The last-mentioned property was unexpected, since dentistry alloys with chromium contents of over 20% in weight lack as a rule the ability to form strong metal-ceramic bonds.

Another point concerns the unaesthetic colorings produced by these high chromium contents during the heat treatments to which dentistry alloys are submitted when associated with ceramic coating materials. In fact, the amount of chromium oxide that forms when the ceramic coating applied to the alloy is fired increases with the chromium content of the alloy; the chromium oxide formed precipitates as coarse interspersed grains which, when present in large numbers, weaken the ceramic-metal bond and confer an unaesthetic coloration to the ceramic coating.

It was found experimentally that despite higher chromium contents (i.e. more than 22% in weight) the alloys of this invention surprisingly do not give rise to the formation of thick chromium oxide layers; consequently, adherence is improved and the ceramic coating applied to the alloy does not take on unattractive colorations. This result is probably due to the presence in the alloy of both silicon and aluminium; the oxides formed by these elements not only limit the thickness of the chromium oxide layer, but also improve its covering power and uniform distribution, thereby promoting a more stable metal-ceramic bond during the firing treatment.

The rare earths content, too, and especially the Ce content, has a positive influence on adherence because the oxides formed by these elements, probably combined with other oxides present, further improve the adherence and evenness of the superficial layer. In particular, it has been noted that this Ce ability is closely dependent on the amount of Ce present in the alloy; in other words, it has been established that a positive influence on adherence is obtained when the Ce content is within the range specified for the alloy according to this invention, while the influence becomes negative for Ce contents above or below the said range. For Ce contents greater than 0.06% in weight, layers of Si compounds are formed that weaken the adherence.

The component elements of the alloy according to this invention confer other specific properties on the alloy that are of great interest to the field of prosthetic dentistry.

For example, the expansion coefficient is a parameter of fundamental importance for dental alloys, especially when the alloys are associated with a ceramic material. The value of this parameter must be around 13.8 to 15.5 $10^{-6}$ $K^{-1}$ for the 25° to 600° C. temperature range; these limits must be strictly observed, for the following reasons: (i) to prevent the formation of cracks and microflaws during solidification of the ceramic material; (ii) to obtain a firm grip of the ceramic material of the finished prosthesis after cooling.

The performance of the alloy of this invention is entirely satisfactory in this respect, since the contents of the various component elements are balanced in such a way as to ensure that the alloy has, in addition to optimal adherence, also an expansion coefficient value in the above-mentioned specified range.

It is worthwhile recalling at this point that the ceramic material must be carefully selected in each case in relation to the type of alloy with which it is to be associated; in fact, different alloys (such as, for example, precious and non-precious alloys) generally exhibit different behaviors for a given ceramic material.

The alloy according to present invention is not only compatible with ceramic materials specified for non-precious alloys, but can also be used with ceramic materials specified for precious alloys since it is characterized by a linear expansion of 0.67% for the 25° to 600° C. temperature range and therefore complies with ADA Specification no. 38; this specification rules that the linear expansion of precious alloys used in association with ceramic materials must be in the 0.61 to 0.69% range.

Dental alloys must also be characterized by a low melting point and by a high fluidity when in the liquid state, so that they are suitable for precision casting of complex shapes. Dental alloys start melting at a temperature of between 1150° and 1200° C, with an optimal melting range of 100°–120° C. The alloy of this invention is characterized by a melting range of about 120° C. in the 1120° to 1280° C. temperature range and is therefore most suitable for prosthetic dentistry uses.

In addition, dental alloys must possess good workability. The ideal hardness for an easily workable alloy is estimated at around 200 to 300 $HV_{10}$ (Vickers 10 hardness scale). The alloy of this invention shows excellent characteristics in this connection too, since it has a hardness number of around 200 to 280 $HV_{10}$.

Similarly, the yield strength $R_{p0.2}$ and the ultimate strength $R_m$ of the alloy must have values which are compatible with good workability; a certain amount of ductility (expressed in terms of the percent elongation A% and preferably kept in the 5 to 10% range) is also desirable, to allow for small-scale adjustments of the finished prosthesis. The alloy of this invention exhibits excellent characteristics also for these parameters, having $A\% \simeq 7-8\%$, $R_{p0.2} \simeq 260$ MPa and $R_m \simeq 500$ MPa.

Finally, of particular importance is the capacity of the alloy to withstand corrosion attack in media simulating the bodily fluids secreted in the mouth, which are used for rating the biocompatibility of alloys for prosthetic dentistry. The behavior of the alloy of this invention, when exposed to these media, showed that it has a stability similar to that of platinum, a metal which is completely resistant to corrosion in the mouth environment.

All the tests carried out on specimens of the alloy of this invention have given results which show that the alloy possesses a well-balanced distribution of optimal properties. In fact, the results in all the tests to which the alloy was submitted were invariably either equal or superior to those obtainable with the best commercial alloys chosen as references.

It can be concluded that the alloy of this invention is definitely superior to all equivalent alloys of this type developed to date.

Three representative compositions (CSM 3, 4 and 5) have been chosen, by way of example, to attest the characteristics of the alloy of this invention. Such compositions are listed in Table I, together with those of six other commercial alloys chosen as references.

TABLE 1

Composition of alloys tested.

| Composition | CSM3 | CSM4 | CSM5 | Alloy 0 | Alloy 1 | Alloy 2 | Alloy 3 | Alloy 4 | Alloy 5 |
|---|---|---|---|---|---|---|---|---|---|
| Cr | 23,60 | 24,50 | 23,95 | 24,40 | 22,80 | 20,34 | 20,20 | 20,90 | 14,3 |
| Mo | 6,50 | 6,25 | 6,32 | 7,11 | 6,80 | 6,29 | 6,00 | 8,7 | 4,8 |
| Si | 3,20 | 3,10 | 3,53 | 3,80 | 1,40 | 7,02 | 4,10 | 0,69 | 0,13 |
| B | 0,30 | 0,33 | 0,31 | 0,33 | 0,46 | 0,20 | 0,60 | — | — |
| Al | 0,005 | 0,005 | 0,135 | 0,260 | 0,095 | 0,045 | 0,013 | — | 2,85 |
| Fe | 0,15 | 0,34 | 0,32 | 0,12 | 0,36 | 1,26 | 0,29 | 0,53 | 0,03 |
| C | 0,01 | 0,02 | 0,01 | 0,03 | 0,07 | 0,05 | 0,07 | 0,023 | 0,023 |
| Cu | 0,25 | 0,25 | 0,50 | n.d. | n.d. | n.d. | 0,007 | — | — |
| Mn | 0,56 | 0,35 | 0,05 | 0,05 | 0,51 | 0,52 | 0,07 | 0,29 | 0,05 |
| S | 0,0015 | 0,0014 | 0,0014 | 0,0018 | — | — | 0,0030 | 0,002 | — |
| Ce | 0,05 | 0,012 | 0,01 | — | 0,75 | 0,11 | — | — | — |
| Y | — | — | — | 0,010 | — | — | 0,070 | — | — |
| Rare Earths | 0,12 | 0,025 | 0,03 | — | — | — | — | — | — |
| V | — | — | — | — | — | — | — | 0,17 | — |
| Nb | — | — | — | — | — | — | — | 3,46 | — |
| Be | — | — | — | — | — | — | — | — | 1,70 |

TABLE 1-continued

Composition of alloys tested.

| Composition | CSM3 | CSM4 | CSM5 | Alloy 0 | Alloy 1 | Alloy 2 | Alloy 3 | Alloy 4 | Alloy 5 |
|---|---|---|---|---|---|---|---|---|---|
| Ti | — | — | — | — | — | — | — | — | 0,30 |

NOTE:
Contents are listed as percent weights. In all cases, the complement percent weight up to 100% consists of Ni and impurities.

MECHANICAL TESTING

Specimens taken from the three compositions of the alloy under this invention and from the reference commercial alloys were characterized by means of mechanical and dilatrometic tests.

Hardness tests at ambient temperature were also carried out on the specimens.

The dilatometric tests were performed at temperatures between 25° and 600° C.

Test results are presented in Table II below.

TABLE II

Mechanical properties.

| Alloy | $HV_{10}$ | $R_{p0,2}$ | Rm | Z % | A % | Melting range °C. | Expansion coefficient $\times 10^{-6} K^{-1}$ |
|---|---|---|---|---|---|---|---|
| CSM 3 | 200 | 266 | 518 | 11 | 8 | 1150–1280 | 14,77 |
| CSM 4 | 210 | 266 | 470 | 11,5 | 6,5 | 1120–1280 | 15,10 |
| CSM 5 | 203 | — | — | — | — | 1120–1280 | 14,30 |
| Alloy 0 | 250 | 354 | 540 | 8,5 | 3,5 | 1130–1250 | 15,50 |
| Alloy 1 | 280 | — | — | — | — | 1350–1400 | — |
| Alloy 2 | 390 | — | 448 | — | — | 1070–1210 | 14,50 |
| Alloy 3 | 315 | — | 650 | — | 4 | 1180–1280 | 15,25 |
| Alloy 4 | 210 | — | — | — | — | — | 14,19 |
| Alloy 5 | 225 | — | — | — | — | — | — |

An explanatory list of the symbols used in Table II is given hereinafter.

$HV_{10}$ = Vickers 10 hardness number
$R_{p0,2}$ = yield strength (0.2 percent permanent set)
Rm = ultimate strength
A% = percent elongation at fracture
Z% = percent area reduction at fracture As can be gathered from the data in Table II, the alloys of this invention are all characterized by optimal hardness (less than 250 $HV_{10}$) and by a low melting range, while the reference alloys exhibit greater hardness and, except for Alloy 2, higher melting ranges and are therefore more difficult to work.

The data also show that the alloys of this invention possess optimal mechanical properties (yield strength, ultimate strength and ductility) in relation to their use for prosthetic dentistry application.

METAL-CERAMIC ADHERENCE

A specimen of one of the alloys of this invention (CSM 3) was melted and cast in a ceramic shell.

The metal-ceramic interface was examined with the scanning electron microscope (fitted with microanalysis equipment) and with the electronic microprobe to verify the existence of a continuous diffusive chemical bond between the components of the alloy and those of the ceramic surface.

The examination confirmed the excellent adherence of the metal to the ceramic surface and the absence of $SiO_2$ or $Cr_2O_3$ layers capable of weakening the bond.

CORROSION RESISTANCE TESTS

Tests were carried out to determine the electrochemical behavior of the alloys of this invention in order to rate their biocompatibility.

The solution adopted for the electrochemical studies was essentially Ringers's artificial saliva, which is used for rating dental alloys and which has the following composition:

9g/l NaCl; 0.25g/l $CaCl_2.6H_2O$; 0.4g/l KCl; 0.2g/l $NaHCO_3$ with PH=7

The following electrochemical tests and measurements were carried out:

(a) determination of the variations in time of the free corrosion potential ($E_c$);

(b) study of potentiodynamic behavior in the −1100 mV to +600 mV range, using a saturated calomel reference electrode (SCE);

(c) measurement of the polarization resistance ($R_p$) which is directly correlated with the corrosion rate of the alloy;

(d) measurement of rate at which $Ni^{+++}$ is released by the alloy in Ringer's solution, for the purpose of establishing the amount of metal that may be absorbed in time by a patient that has a Ni-Cr dental prosthesis.

A brief description will now be given of each test and of the results obtained.

(a) The free corrosion potential ($E_c$) was measured on virgin alloy specimens in an electrochemical cell under the following experimental conditions:

solution: Ringer's solution deareated with $N_2$
normal physiological conditions: T=37° C., pH=7
reference electrode: saturated calomel (SCE)
preliminary polishing of specimens with grade 1000 abrasive paper.

The variations of the free corrosion potential ($E_c$) were determined over a 1000 minute period of exposure for each alloy tested. The corrosion potential readings made 180 minutes after the start of the test (this duration is generally sufficient for reaching conditions of equilibrium) are listed in Table III, together with the variations measured over the remaining period of exposure up to the end of the test.

TABLE III

Corrosion potentials ($E_c$) measured after 180 minutes of exposure to deareated Ringer solution at 37° C. with pH = 7 and variations of said potential values recorded during remaining period of exposure.

| Alloy | $E_c$ after 180 min · mV/SCE | Subsequent variation of $E_c$ mV |
|---|---|---|
| Alloy 1 | −400 | ±50 |
| Alloy 2 | −420 | ±50 |
| CSM 3 | −340 | ±5 |
| Alloy 5 | −270 | ±30 |
| Alloy 4 | −280 | ±100 |
| Alloy 3 | −340 | ±60 |

The data of Table III show that the alloy of this invention has a far greater stability in time than any of the other alloys tested and that it occupies an intermediate position among the other alloys as far as its equilibrium potential is concerned. In brief, equilibrium is reached rapidly and the potential value then remains practically unaltered in time. This indicates good corrosion behavior.

(b) A number of potentiodynamic scans from −1100 mV/SCE to +600 mV/SCE were performed on the CSM 3 alloy under the same experimental conditions adopted for the tests under point (a) above and according to the following procedure:

activation: −1100 mV/SCE for 3 minutes
start of scan: from −1100 mV/SCE
scanning rate: 2.4V/h The voltage-current curve plotted for the CSM3 alloy specimen (previously remelted in the dental laboratory, submitted to the heat treatments required for sintering the ceramic portions and finally cleaned with the tools and according to the standard practice of dental technicians) evidences that the alloy has a very wide stability range, up to a potential of +500 mV/SCE, which is similar to that of platinum, a metal completely resistant to corrosion in the mouth environment.

(c) Starting from the corrosion potential value, a limited potentiodynamic scan (+20 mV) was carried out under the same experimental conditions as the preceding two tests in order to determine:

the polarization resistance ($R_p$) of the alloy, expressed as the ratio of the potential variation (limited to 10÷15mV) to the current producing the variation (DV/Di);

the corrosion rate expressed in mm per year.

With these data it was possible to quantify the tendency of the alloys to corrode, since was known the higher Rp the greater the corrosion resistance of the alloy.

The values measured on the various virgin alloy specimens tested after 8-10 minutes of exposure are listed in Table IV.

TABLE IV

Polarization resistance ($R_p$) and corrosion rate (CR) of virgin dental alloys.

| Alloy | Average $R_p$ (KΩ) | Average CR (mm/yr) |
|---|---|---|
| Alloy 3 | 187.5 | $15 \cdot 10^{-4}$ |
| Alloy 2 | 281.25 | $11 \cdot 10^{-4}$ |
| CSM 3 | 437.5 | $6 \cdot 10^{-4}$ |
| Alloy 4 | 337.5 | $8 \cdot 10^{-4}$ |

As can be gathered from the data of Table IV, the alloy of this invention has a superior corrosion resistance compared to the other reference alloys, since it has a lower corrosion rate and a higher polarization resistance.

(d) The alloys of this invention are all Ni-based alloys, an element which is considered a potential allergene since, in concentration above certain limits (which have not yet been fully determined and are dependent on individual response), it can induce allergic states in human organisms.

Tests were therefore arranged to establish the rate at which this element was released by the alloy under simulated physiological conditions.

The tests were carried out on virgin alloy specimens in Ringer's solution at the temperature of 37° C., adopting the following pH values:

pH=5, to simulate infection
pH=7, to simulate normal physiological conditions
pH=9, to simulate tumefaction.

The specimens were placed in individual chemically inert polyethylene containers filled with Ringer's solution and the containers kept at the constant temperature of 37° C. in a water bath. Small amounts of the solution were taken from each container at pre-determined time intervals and analyzed for $Ni^{+++}$ by means of the plasma emission spectrometry technique. The amounts of $Ni^{+++}$ released by each of the alloys tested, after 30 days of exposure, are listed below in g/cm².

| Alloy 3 | Alloy 1 | Alloy 2 | CSM 3 | |
|---|---|---|---|---|
| 240 | 270 | 50 | 10 | at pH = 5 |
| 50 | 150 | 30 | 7 | at pH = 7 |
| 45 | 25 | 25 | 7 | at pH = 9 |

Note the definite improvement in the values when passing from the reference alloys to the CSM 3 alloy, which exhibits a very great stability.

The data also show that the higher amounts are released under abnormal physiological conditions (i.e. in the presence of infection and of a lowering of the physiological pH value), while the values remain at very low levels under normal or tumefaction conditions.

We claim:

1. Alloy for dental prostheses consisting essentially of:

| | |
|---|---|
| Cr | 22.0-25.0% weight |
| Mo | 5.5-7.5% weight |
| Si | 2.0-4.5% weight |
| B | 0.25-0.50% weight |
| Al | ≦0.2% weight |
| Fe | ≦0.5% weight |
| C | ≦0.05% weight |
| Cu | ≦0.5% weight |
| Mn | ≦0.5% weight |
| S | ≦0.01% weight |
| Rare earths | 0.005-0.2% weight |
| remainder Ni and impurities. | |

2. Alloy according to claim 1 comprising:

| | |
|---|---|
| Cr | 23.5-24.5% weight |
| Mo | 6.2-7.2% weight |
| Si | 3.0-4.0% weight |
| B | 0.30-0.4% weight |
| Al | 0.005-0.1% weight |
| Fe + Mn + Cu | 1% weight |
| C | 0.03% weight |
| S | 0.01% weight |
| Rare earths | 0.005-0.15% weight |

-continued

| remainder Ni and impurities. |

3. Alloy according to claim 1, characterized in that the rare earths contain Ce fractions ranging between 0.01% to 0.06% in weight.

4. Alloy acording to claim 1, characterized in that the contents of certain specific component elements are expressed by the following mathematical relationships:

(a) $xCr + 3.3yMo \geq 42$ where:
x = percent weight of chromium present in the alloy
y = percent weight of molybdenum present in the alloy;

(b) $1 < \text{rare earths}/S < 40$.

5. Alloy according to claim 4, characterized by the following compositional ratio: $10 < \text{rare earths}/S < 30$.

6. Alloy according to claim 3, characterized by the following composition ratio: $1 < Ce/S < 30$.

* * * * *